(12) United States Patent
Grosland et al.

(10) Patent No.: US 11,026,828 B2
(45) Date of Patent: *Jun. 8, 2021

(54) CLUBFOOT ORTHOTIC

(71) Applicant: University of Iowa Research Foundation, Iowa City, IA (US)

(72) Inventors: Nicole M. Grosland, Iowa City, IA (US); Jose Morcuende, Iowa City, IA (US); Thomas M. Cook, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 254 days.

This patent is subject to a terminal disclaimer.

(21) Appl. No.: 16/102,523

(22) Filed: Aug. 13, 2018

(65) Prior Publication Data

US 2019/0076285 A1 Mar. 14, 2019

Related U.S. Application Data

(63) Continuation of application No. 14/403,849, filed as application No. PCT/US2013/031999 on Mar. 15, 2013, now Pat. No. 10,045,874.

(60) Provisional application No. 61/651,850, filed on May 25, 2012.

(51) Int. Cl.
*A61F 5/00* (2006.01)
*A61F 5/01* (2006.01)
*A43B 13/28* (2006.01)
*A43B 7/00* (2006.01)

(52) U.S. Cl.
CPC .............. *A61F 5/0127* (2013.01); *A43B 7/00* (2013.01); *A43B 13/28* (2013.01); *A61F 5/0193* (2013.01); *Y10T 29/49826* (2015.01)

(58) Field of Classification Search
CPC .. A61F 5/14; A61F 5/04; A61F 5/0585; A61F 5/05841; A61F 5/05825; A61F 5/3715; A61F 5/3723; A61F 5/373; A61F 5/0127; A61F 5/0113; A61F 5/0116
USPC .......... 602/29, 28, 27; 36/140, 142, 144, 160
See application file for complete search history.

(56) References Cited

U.S. PATENT DOCUMENTS

| | | | |
|---|---|---|---|
| 2,482,646 A | 9/1949 | Brachman et al. | |
| 2,787,263 A | 4/1957 | Beard | |
| 2,920,620 A * | 1/1960 | Rogers | A61F 5/0193 602/24 |
| 4,040,416 A * | 8/1977 | Zentman | A61F 5/0193 602/24 |
| 4,263,901 A * | 4/1981 | Nichols | A61F 5/0193 602/24 |
| 4,550,722 A | 11/1985 | Kurtz et al. | |
| 4,606,334 A | 8/1986 | Salmon | |
| 7,267,657 B1 | 9/2007 | Mitchell | |
| 7,850,631 B2 | 12/2010 | Mitchell | |
| 10,045,874 B2 | 8/2018 | Grosland et al. | |
| 2007/0000500 A1* | 1/2007 | Richard | A61F 5/3715 128/869 |

(Continued)

FOREIGN PATENT DOCUMENTS

DE 20319325 U1 4/2004
WO WO-2009064189 A1 5/2009

*Primary Examiner* — Rachael E Bredefeld
*Assistant Examiner* — Adam Baker
(74) *Attorney, Agent, or Firm* — Foley Hoag LLP; Stephen J. Kenny

(57) ABSTRACT

Devices and methods for treating clubfoot are disclosed.

19 Claims, 10 Drawing Sheets

(56) References Cited

U.S. PATENT DOCUMENTS

2007/0073206 A1  3/2007  Hatton et al.
2007/0142760 A1* 6/2007  Mitchell ............... A61F 5/0193
                                              602/29
2009/0082180 A1  3/2009  Castellano

* cited by examiner

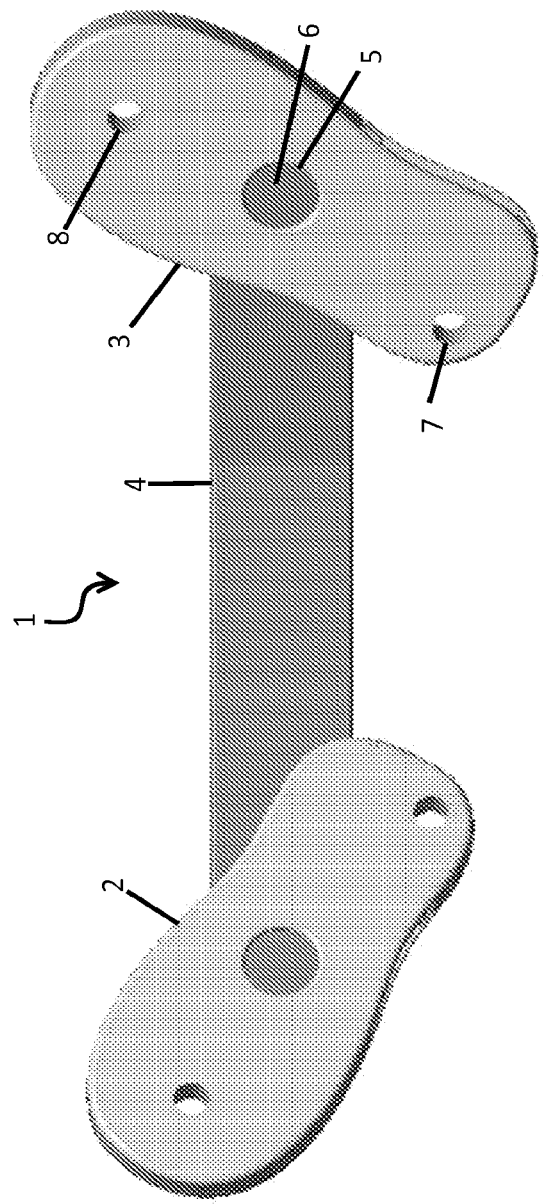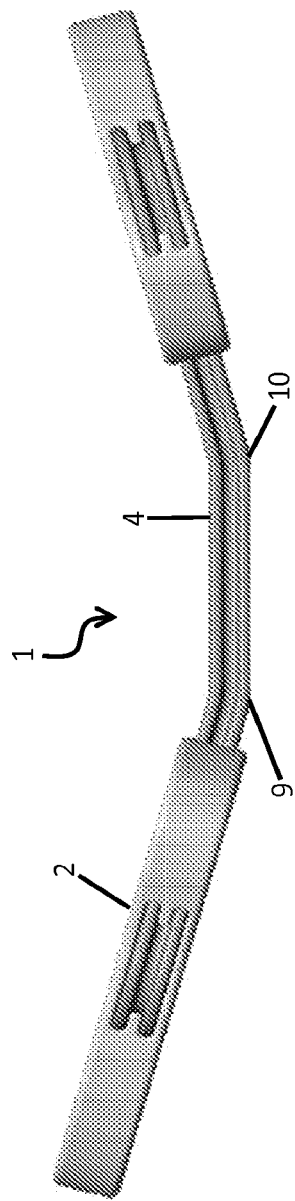

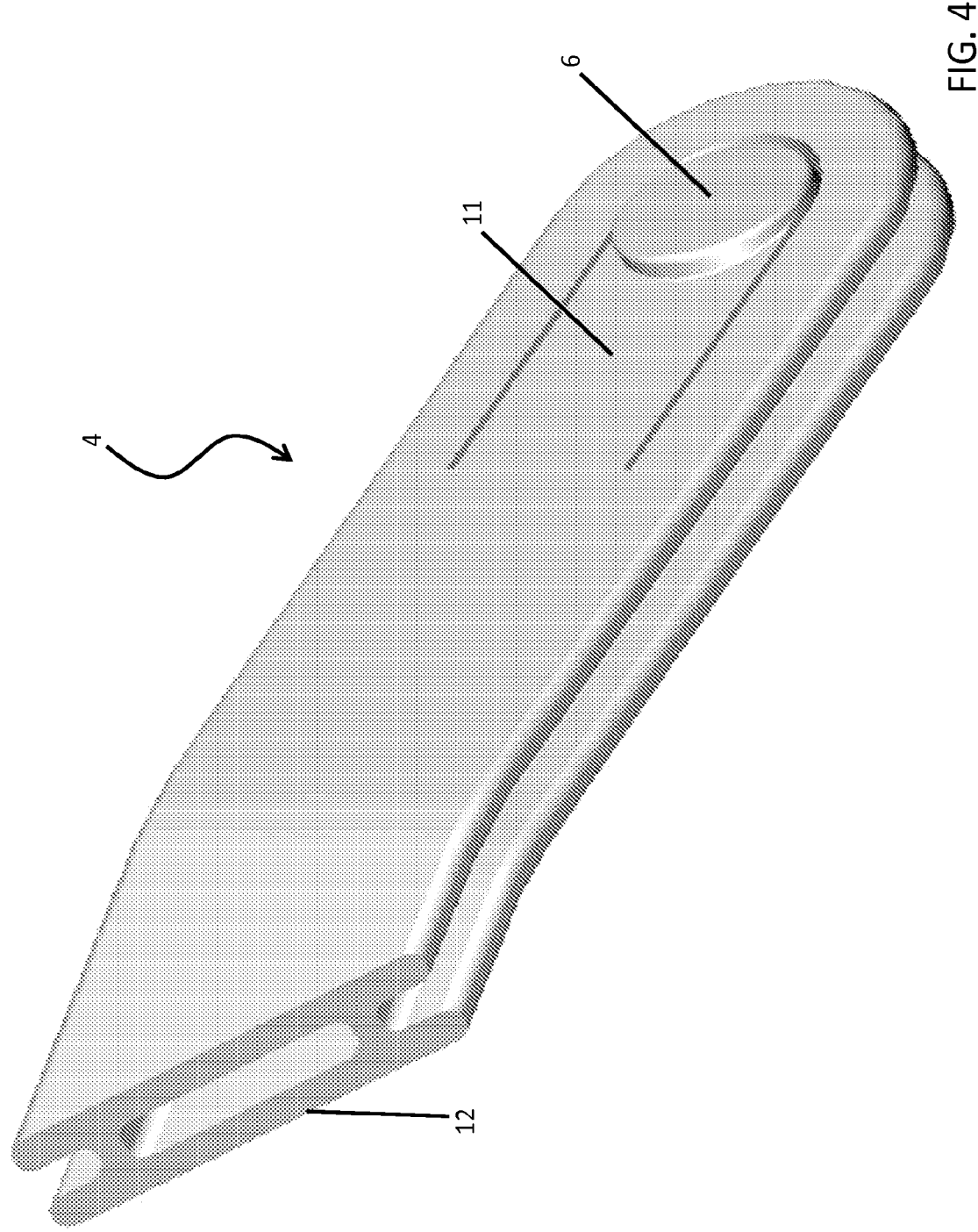

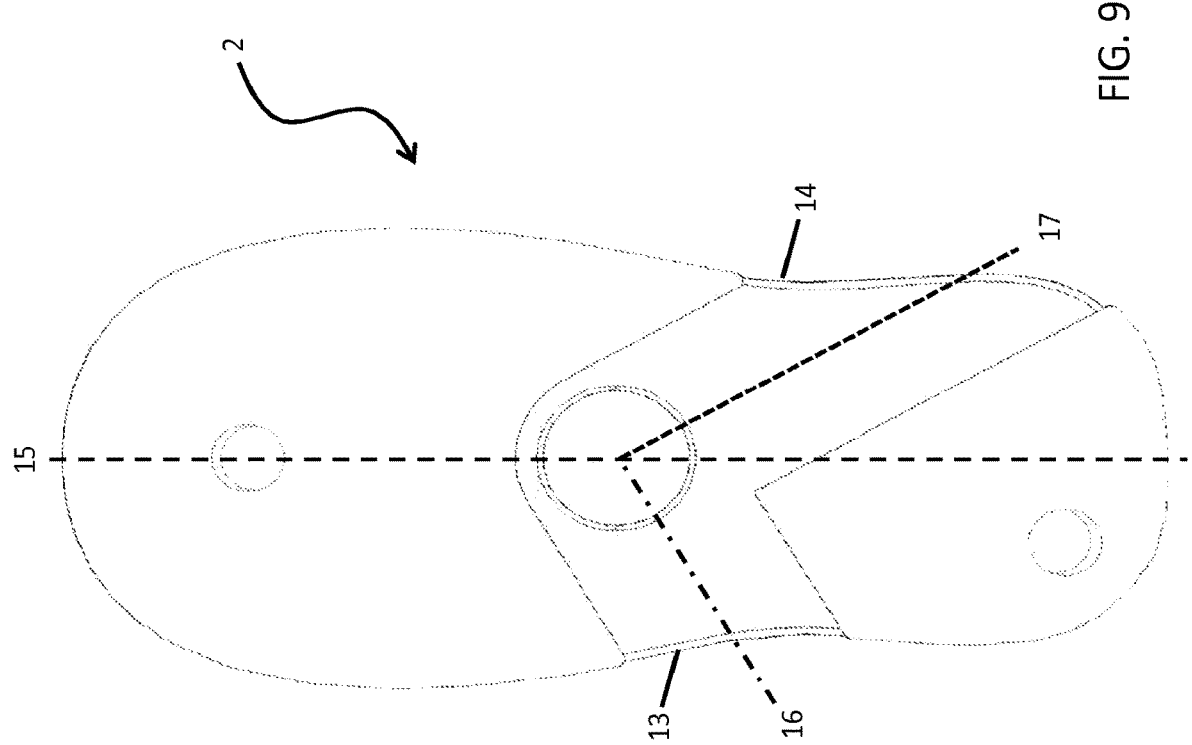

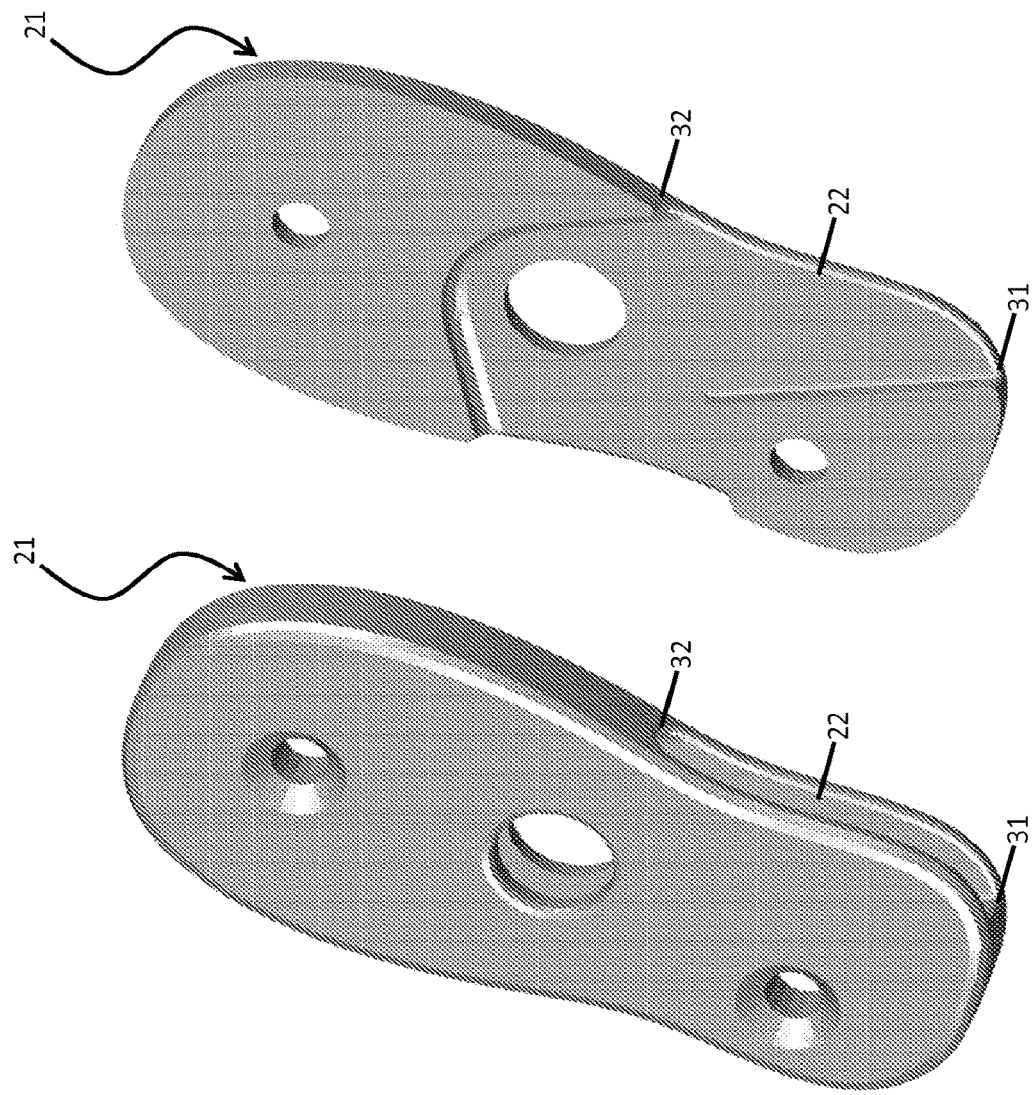

CLUBFOOT ORTHOTIC

RELATED APPLICATIONS

This application is a Continuation of and claims priority under 35 USC 120 to U.S. application Ser. No. 14/403,849 filed Nov. 25, 2014, which is the U.S. national stage of, and claims priority to, International Patent Application number PCT/US2013/031999 filed 15 Mar. 2013, which claims the benefit of priority to U.S. Provisional Patent Application Ser. No. 61/651,850, filed 25 May 2012, all of which are hereby incorporated herein by reference in their entirety.

SUMMARY

Devices and methods for treating clubfoot are disclosed.

BRIEF DESCRIPTION OF THE DRAWINGS

FIG. 1 schematically shows a device for treating clubfoot, viewed from above.

FIG. 2 schematically shows the same device as FIG. 1, viewed from behind.

FIG. 4 schematically shows a cross-sectioned close-up of the bar portion shown in FIG. 3.

FIG. 9 schematically shows a face-on cross-section of a platform portion of the device shown in FIG. 1.

FIG. 11 schematically shows another platform portion.

FIG. 12 schematically shows a cross-section of the platform portion shown in FIG. 11 shown in the same perspective as FIG. 11.

DETAILED DESCRIPTION

Figure 3:
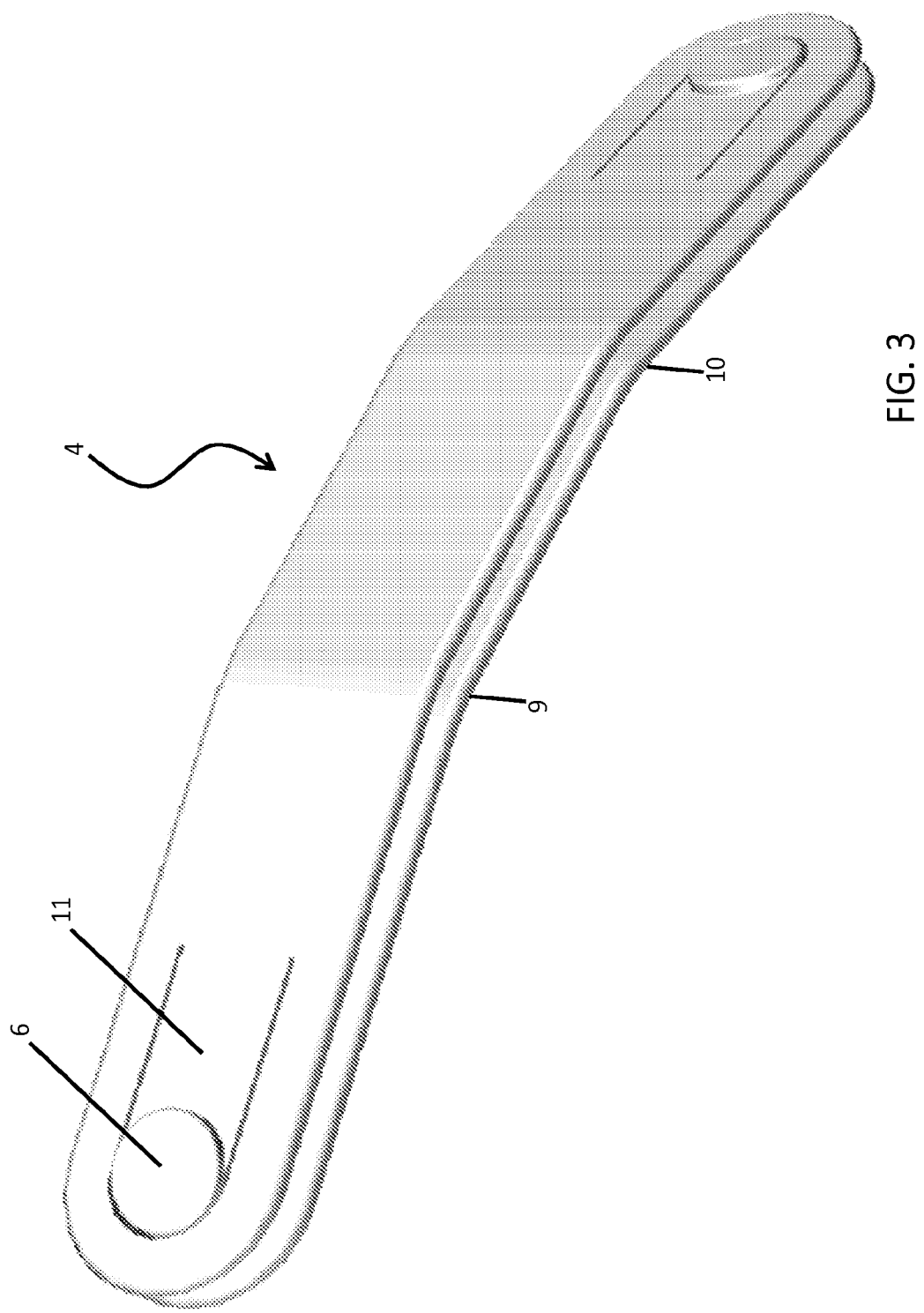
FIG. 3 schematically shows a bar portion of the device of FIG. 1.

FIGS. 1-13 schematically show various aspects of a device for treating clubfoot. In use, a pair of shoes fitted to the user's feet will be attached to the device and worn by the user. The device is simple to use and adjust, with a minimum of possible settings. When in use, the device allows for no motion, neither translation nor rotation, of the user's feet relative to one another. Advantages of the device include simplicity and limited adjustability, thereby facilitating use by relatively untrained users. A device like the one shown schematically in FIGS. 1-13 may be ideal for use in the developing world. The simplicity of the design can result in low manufacturing costs. And because the device is simple to use, it does not require careful adjustment by a trained medical professional, whose services may be difficult to obtain in developing communities.

FIG. 1 schematically shows one embodiment of a device 1 for treating clubfoot. The device shown in FIG. 1 includes two identical platforms 2, 3 and a bar 4. Each platform 2, 3 includes two slots (not visible in FIG. 1) into which the bar can be inserted (described in detail below). Each platform also has a locking hole 5 that mates with a push-button 6 on the bar 4. Each platform 2, 3 also includes shoe-attachment holes 7, 8 for securing a shoe to the platform. FIG. 1 shows the device 1 from the point of view of a user looking down on the device as if it were positioned on the ground in front of a standing user.

FIG. 2 schematically shows the same device 1 from behind. As shown, the bar 4 has two bends 9, 10 of about 15 degrees. When in use, a shoe will be attached to each platform, attached, for example, with a rivet or screw through shoe-attachment holes 7, 8. The position and orientation of the user's shoes and feet with the desired external rotation (i.e., turn-out, in this embodiment either 30 or 60 degrees) and/or pronation/dorsiflexion (in this embodiment, 15 degrees) will be determined by the orientation of the platforms 2, 3 relative to the bar 4, and also by the shape of the bar 4 itself.

FIG. 3 schematically shows the bar 4 in more detail. The push-button 6 is shown at the end of a cantilever 11. The bar may be formed of an elastic material that allows the cantilever to bend. In this way, the user can depress the push-button 6 out of the locking-hole 5, allowing the bar 4 to be removed from the slots in the platforms 2, 3. Similarly, the bar 4 can be inserted into the slot by depressing the button 6 and advancing the bar 4 until the button 6 snaps into the hole 5.

In alternative embodiments the desired degree of pronation/dorsiflexion can be achieved with only one bend in the center of the bar rather than two bends. Or the bar may have a continuous curve rather than one or two discrete angles. Alternatively the bar may be flat and essentially planar (lying essentially in the transverse plane) so as to achieve pronation/dorsiflexion of 0 degrees.

The bar may also curve or include discrete angled bends in another direction so as to produce external rotation, or turn-out.

FIG. 4 shows a close-up of the same bar 4 cut to show a cross-section 12. In this embodiment the bar 4 has an I-shaped cross-section 12, designed to mate with corresponding features inside the slots defined by the platforms. Any of a variety of cross-sectional shapes may be used as long as the shape mates with the complementary shape defined by the slot.

Figure 6:
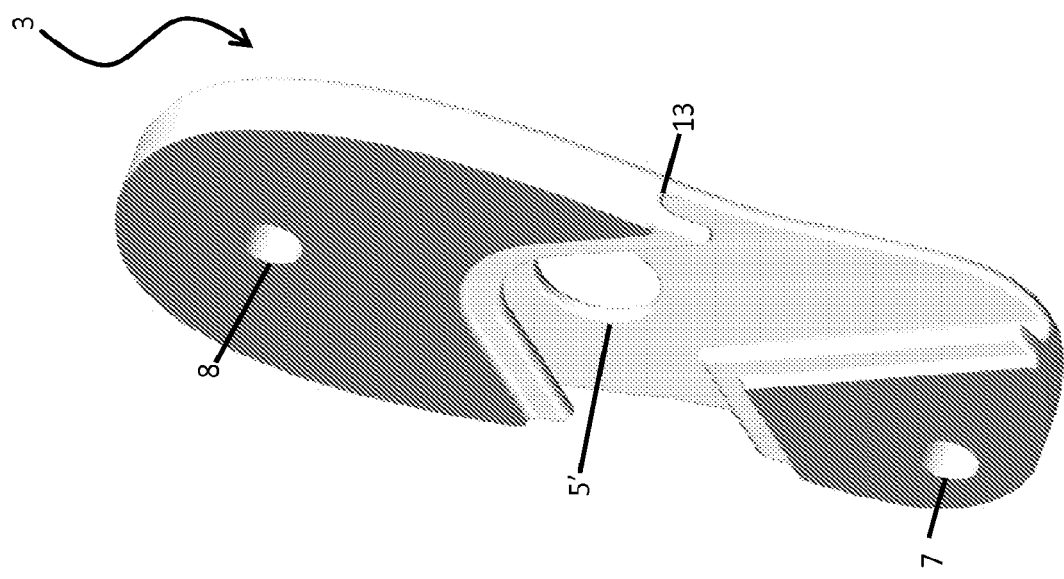
FIG. 6 schematically shows a cross-section of the platform portion shown in FIG. 5 in the same perspective as FIG. 5.
Figure 5:
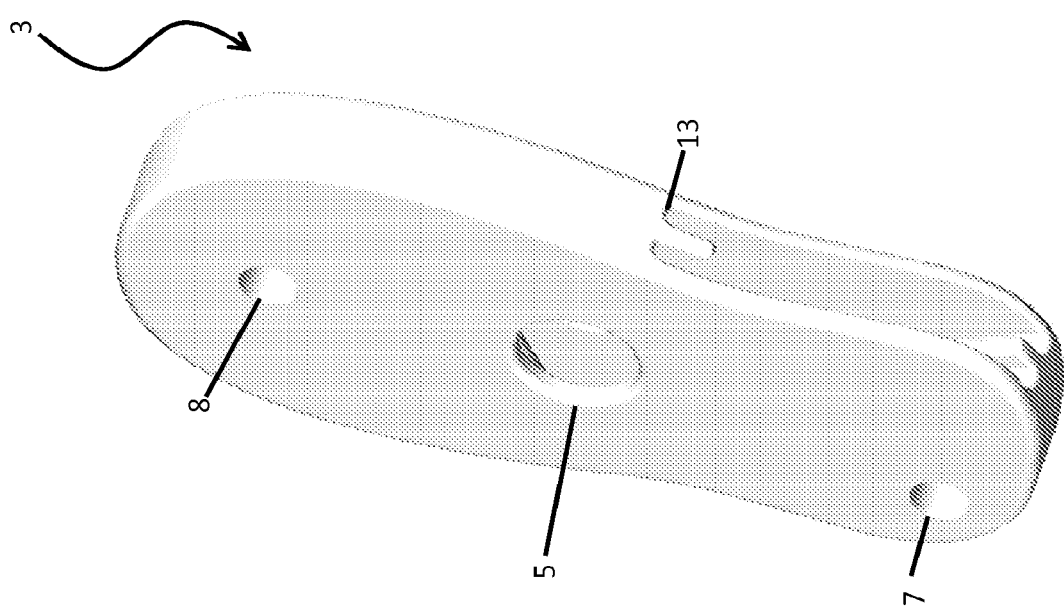
FIG. 5 schematically shows a platform portion of the device of FIG. 1.
Figure 8:
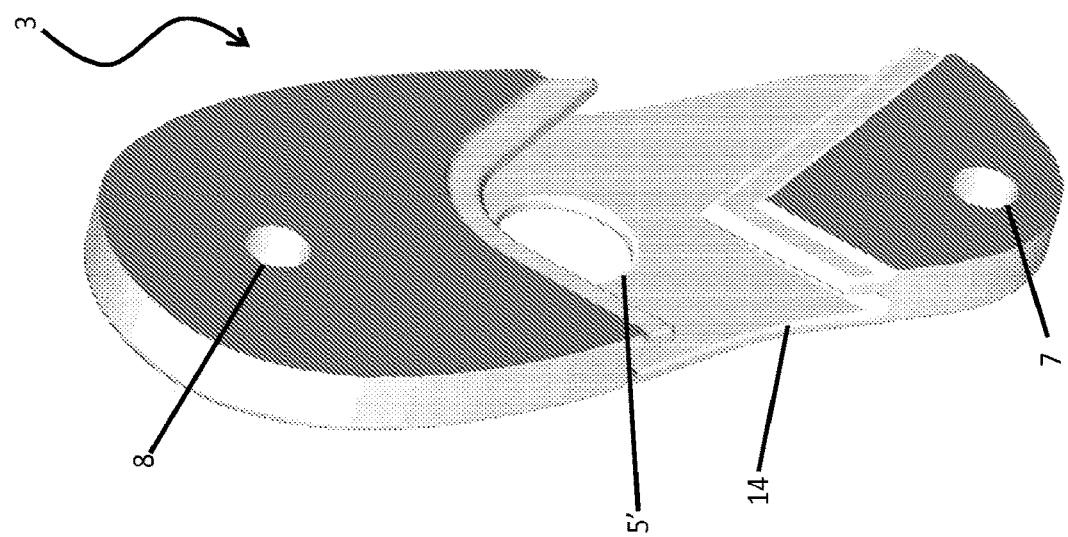
FIG. 8 schematically shows a cross-section of the platform portion shown in FIG. 7 in the same perspective as FIG. 7.
Figure 7:
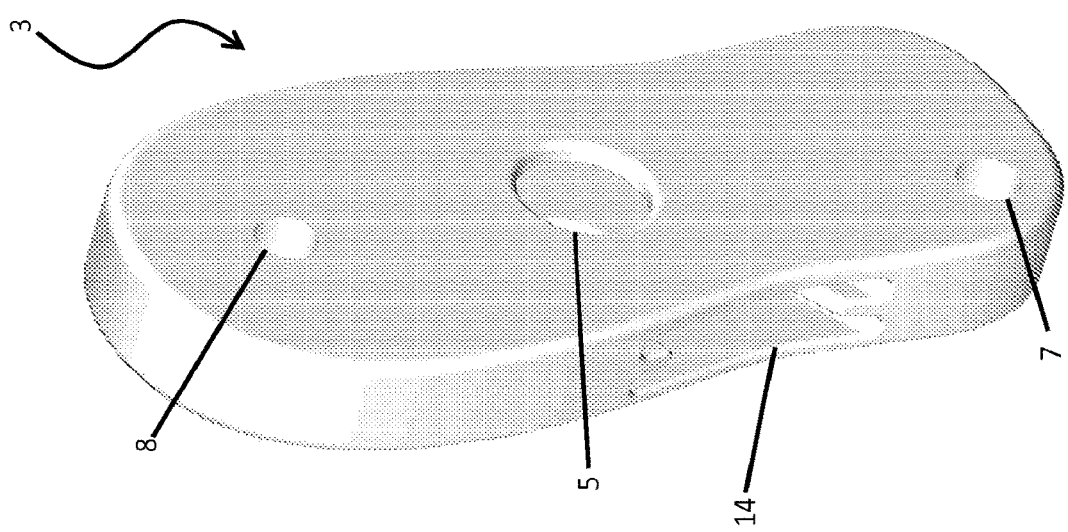
FIG. 7 schematically shows the platform portion shown in FIG. 5 in a different perspective.

FIGS. 5-8 schematically show a platform 3 in its entirety and in cross-section in each of two perspective views. FIGS. 5 and 7 show the locking-hole 5 while the cross-sections in FIGS. 6 and 8 show an identical locking-hole 5' on the opposite face of the platform 3. Identical locking holes 5, 5' allow the user to flip the platform 3 upside down and still lock the platform 3 to the bar 4 with the same button 6. The vertically symmetrical I-beam cross-sectional shape of the bar 4 also facilitates flipping the platform 3 vertically, although any cross-sectional complementary shapes with vertical mirror symmetry would work. FIGS. 5-8 all show the shoe-attachment holes 7, 8. In FIG. 5, one of the two slots in the platform 3, the 60-degree slot 13, is visible. When the bar is inserted into the 60-degree slot 13, the platform is oriented so as to position the foot with 60 degrees of external rotation, that is, with a 60-degree turnout. FIG.

6 schematically shows the platform 3 from the same perspective as FIG. 5, cross-sectioned.

FIGS. 7 and 8 schematically show the same platform 3 from another perspective so that the other slot, the 30-degree slot 14, is visible. When the bar is inserted into the 30-degree slot 14, the platform is oriented so as to position the foot with 30 degrees of external rotation, that is, with a 30-degree turnout.

FIG. 9 schematically shows a face-on cross-section of the platform 2. The anterior-posterior axis 15 is shown as a dashed line. The axis 16 of the 30-degree slot 13 is shown as a dash-dotted line. The axis 17 of the 60-degree slot 14 is shown as a dotted line. FIGS. 1 and 2 show a fully assembled device with one platform 2 in the 60-degree turn-out position and the other platform 3 in the 30-degree turn-out position. Each slot 13, 14 leads to a channel aligned along the corresponding axis 16, 17. The bar fits into either channel as it is advanced into the slot. The I-shaped edges of the bar mate with the complementary internal shape of the channel.

Figure 10:
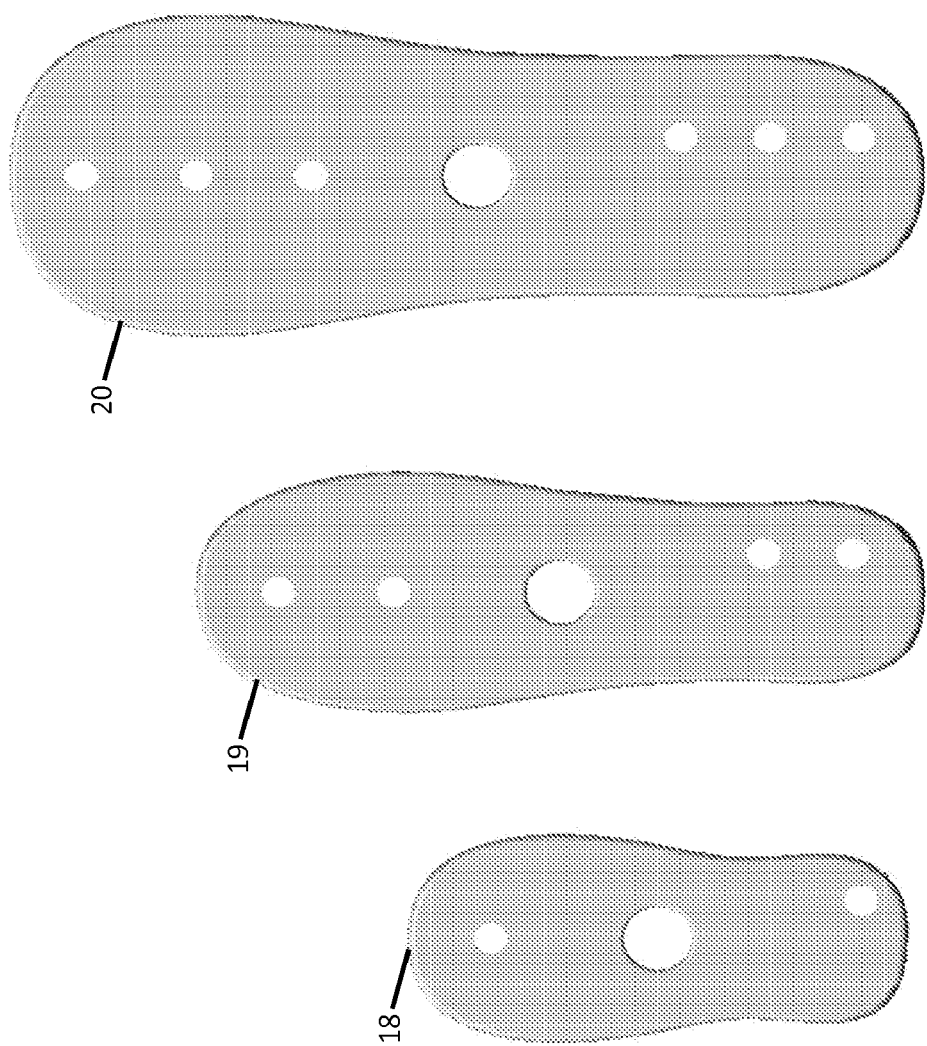
FIG. 10 schematically shows three different platforms of varying sizes compatible with a device such as is shown in FIG. 1.

FIG. 10 schematically shows three different platforms 18, 19, 20, of varying size. Different platforms may be used with different sized shoes, as for larger or smaller patients, or for accommodating the growth of a single patient over time. Similarly, different sized bars can be provided depending on the size of the patient. As shown, some shoe-attachment holes are located on the anterior-posterior axis of the platform, while others are not. In some embodiments, shoe attachment holes may also be located so that, when the platform is flipped over (i.e., rotated 180 degrees about the anterior-posterior axis), the shoe attachment holes line up with corresponding holes in the user's shoes. Or the shoe attachment holes may be located asymmetrically as shown.

An advantage of the device shown in FIGS. 1-9 is its simplicity. For example, there is a minimum of adjustability in the device. Each platform is attached to the bar by simply sliding the bar into one of the platform's two slots. The orientation of the slot fully determines the orientation of the platform relative to the bar. There are only two choices for how to orient each platform, for example 30-degree or 60-degree turn-out as shown in the figures. Other angles are possible for manufacture. As drawn, the axes 16, 17 of the slots 13, 14 happen to be perpendicular to each other. But the axes need not be perpendicular if a different pair of angles is desired.

Furthermore, because the platforms 2, 3 are identical and reversible, there is no dedicated right-foot platform and left-foot platform. Either platform 2, 3 can be used for either foot in either the 60-degree or 30-degree orientation. In FIG. 1, the device is arranged so that the patient's left foot and shoe, attached to the left platform 2, will be in the 60-degree turn-out position, while the patient's right foot and shoe, attached to the right platform 3, will be in the 30-degree turn-out position. If a user wants to adjust the device so that the left-foot turn-out is 30-degrees instead of 60-degrees, the user detaches the platform 2 by removing the bar 4 from the 60-degree slot, rotates the platform 2 180 degrees about the anterior-posterior axis 15, and inserts the bar 4 into the 30-degree slot. Likewise, to reorient the right foot from 30-degree turn-out to 60-degree turn-out, the user detaches the platform 3 by removing the bar 4 from the 30-degree slot, rotates the platform 3 180 degrees about the anterior-posterior axis 15, and inserts the bar 4 into the 60-degree slot. Because the platforms 2, 3 are identical and reversible, it is impossible to put a platform on the "wrong" side. Either platform can be a right or left platform in either of the two possible orientations.

The bar 4 is also designed to be easily attached to and detached from each of the platforms 2, 3. As shown, the bar 4 locks into the platform by way of a push-button 6 that mates with a locking-hole 5, but other lock and release mechanisms are possible as well. The I-beam cross-sectional shape of the bar 4 also helps to stabilize the bar 4 in a slot by providing complementary tongues and grooves. Other cross-sectional shapes are possible as well, as long as the shape of the bar 4 mates with the shape of the slots.

Figure 13:
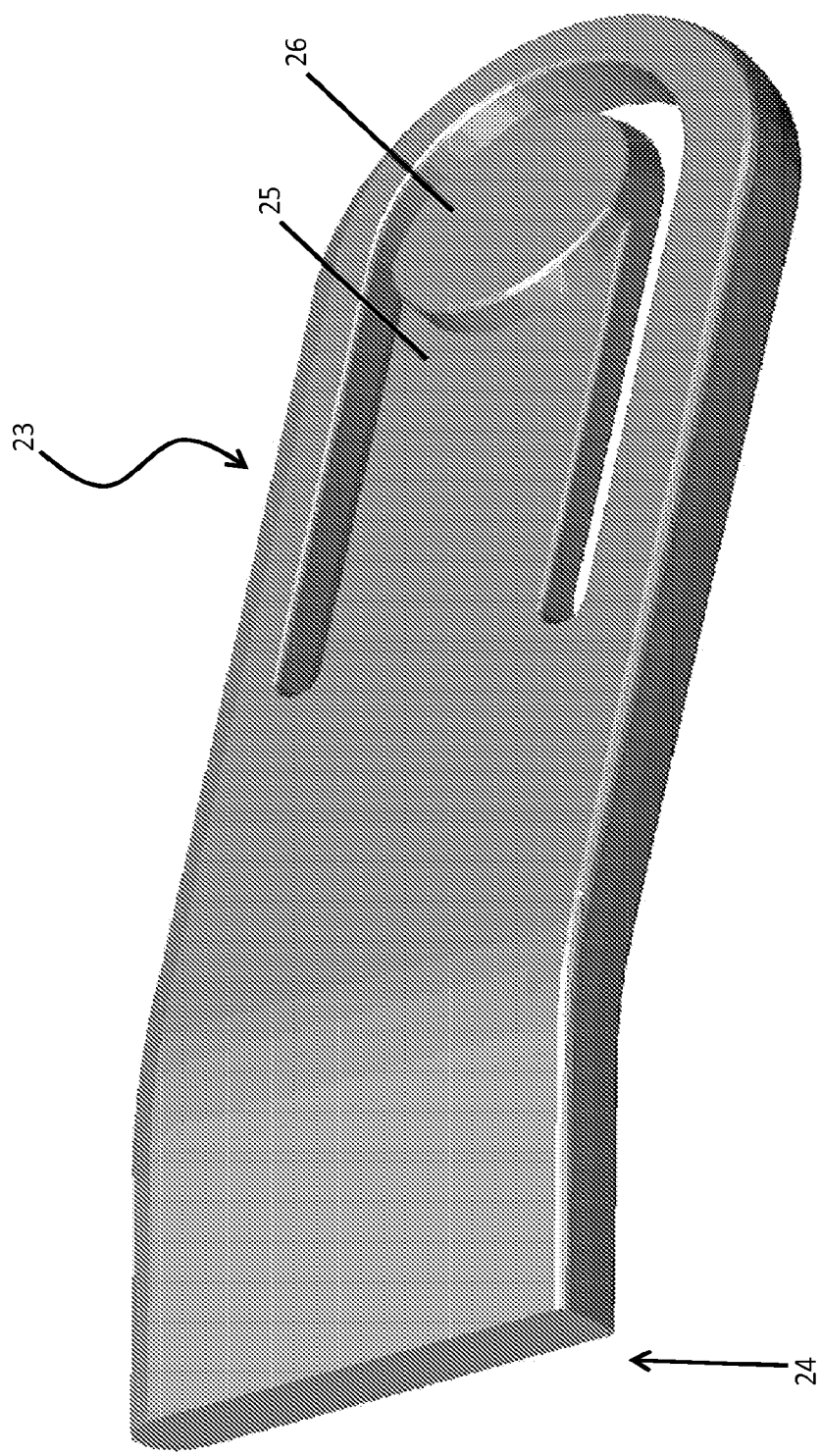
FIG. 13 schematically shows a cross-sectioned close-up of a bar portion designed to mate with the platform of FIG. 11.

FIG. 11 schematically shows a platform 21 similar to the platforms shown in FIGS. 5-10, but having a differently shaped slot 22. The slot 22 has no I-beam structure as in the embodiment of FIGS. 3 and 4. Instead, the slot 22 has a square profile at the rear end 31, and a rounded profile at the front end 32. FIG. 12 schematically shows the same platform 21 with slot 22 in cross-section. FIG. 13 shows a cross-sectioned close-up of a bar 23 designed to mate with the slot 22 shown in FIGS. 11 and 12. The bar 23 has a cross-sectional shape 24 that matches the slot 22, generally flat, squared at one end and rounded at the other end. The bar 23 is shown with the same sort of cantilever 25 and push-button 26 as the bar shown in FIGS. 1-4. By making the mating shapes of the bar and slot asymmetrical so as to distinguish front from back on both the slot 22 and the bar 23, it is impossible for a user to insert the bar upside down with the button 26 facing down. The same effect could be accomplished by making the bar vertically asymmetrical so as to distinguish top from bottom.

Figure 14:
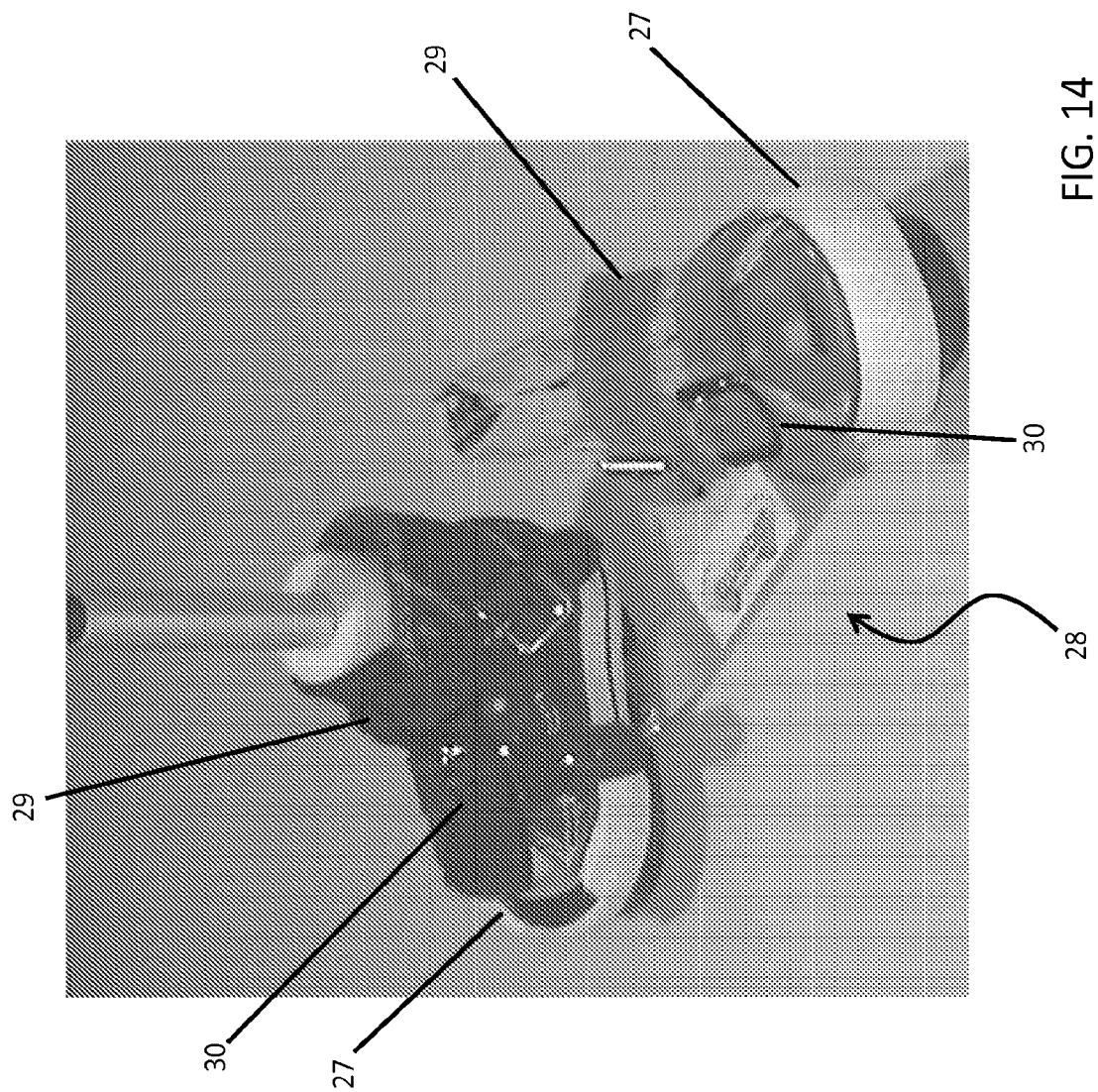
FIG. 14 is a photograph of one particular embodiment of a clubfoot brace including shoes.

Shoes may be attached to the platforms in a wide variety of ways including rivets, screws, or nuts and bolts, or the like that pass through the sole of the shoe and also through a hole on the platform. Platforms may also include straps or clips for attachment to the outside of a shoe, as on some roller skates. Shoes could be attached using a hook and loop fastener such as Velcro™. An example is shown in FIG. 14, in which children's shoes 27 are attached to a version of the device 28 by screws and t-nuts (not visible). The shoes are to be secured to the user's feet with buckles 29, 30. The shoes could be unmodified children's shoes strapped onto the platform, or they could be modified to have a bolt pass through the sole, or to have the platform attached to the shoe in some other way. In other embodiments the platform, including its slots could be integrally formed with the sole of a shoe. In such embodiments, of course, the platform cannot be switched between the user's left and right because a left shoe cannot become a right shoe. Nor can the platform simply be flipped over and used in a different orientation, since the shoe must be facing upward to receive the user's foot.

In other embodiments, each platform could have only one slot, so that only one degree of turnout was possible. Or each platform can have two slots both of which result in the same turnout when attached to a bar. As shown in the figures, the two slots in a given platform correspond to two different degrees of turnout. Alternatively, or additionally, slots could be angled out of the transverse plane so that the different slots could result in different degrees of pronation.

In another alternative, a platform can include a tab rather than a slot, while the bar can have a slot to receive the tab. The slot in the bar and the tab protruding from the platform would be designed to mate just like the bar and slots shown in FIGS. 1-13. In such embodiments, the protrusion from the platform can include a cantilever and push-button arrangement similar to that shown in FIG. 3, while the bar can include a locking hole to receive the push-button.

The devices like those shown schematically in FIGS. 1-13 could be used to treat clubfoot in patients that have already completed a Ponseti-type successive casting treatment.

A kit for treating clubfoot in a patient can include a first platform, a second platform, and a bar having a first end and a second end. The first platform can define a first slot sized and shaped to mate with the first end so that when the first slot mates with the first end, (a) the first platform is fixedly attached to the bar with a predetermined first orientation relative to the bar, and (b) the first platform can neither rotate nor translate relative to the bar. The second platform can define a second slot sized and shaped to mate with the second end so that when the second slot mates with the second end, (a) the second platform is fixedly attached to the bar with a predetermined second orientation relative to the bar, and (b) the second platform can neither rotate nor translate relative to the bar. The first and second platform can both be sized and shaped to substantially match the size and shape of the sole of a shoe of the patient.

The first platform can further define a third slot sized and shaped to mate with the first end so that when the third slot mates with the first end, (a) the first platform is fixedly attached to the bar with a predetermined third orientation relative to the bar, and (b) the first platform can neither rotate nor translate relative to the bar. The second platform can further define a fourth slot sized and shaped to mate with the second end so that when the fourth slot mates with the second end, (a) the second platform is fixedly attached to the bar with a predetermined fourth orientation relative to the bar, and (b) the second platform can neither rotate nor translate relative to the bar.

The first platform can have a heel end and a toe end defining a platform axis between the heel end and the toe end. The first slot can open on one side of the platform axis and the third slot can open on the opposite side of the platform axis. In addition, the first and second orientations can be equal so that, if the first slot is mated to the first end and the second slot is mated to the second end, and the assembled platforms and bar define a bar axis between the platforms, then the external rotation of the platforms relative to the bar axis is the same for both platforms. Likewise, the third and fourth orientations can be equal so that if the third slot is mated to the first end and the fourth slot is mated to the second end, and the assembled platforms and bar define a bar axis between the platforms, then the external rotation of the platforms relative to the bar axis is the same for both platforms.

The bar can include a flexible first cantilever adjacent to the first end, the first platform can define a locking hole, and the cantilever can be sized and shaped to mate with a first locking hole when the first slot mates with the first end.

The bar can be non-planar. The bar can be essentially planar. The bar can include two discrete bends. The bends can equal in angle. The angle could be 15 degrees.

The first and second orientations can be equal so that, if the first slot is mated to the first end and the second slot is mated to the second end, and the assembled platforms and bar define a bar axis between the platforms, then the external rotation of the platforms relative to the bar axis is the same for both platforms.

The first and second platforms can be substantially identical.

The cross-sectional geometry of the first end is substantially identical to the cross-sectional geometry of the second end and the cross-sectional geometry of the first slot can be substantially identical to the cross-sectional geometry of the slot end, so that the first and second slots are each sized and shaped to mate with either of the first or second ends. Or the first end can have a cross-sectional geometry that is front to back mirror asymmetric.

A device for treating clubfoot in a patient can be formed from any of the above kits by mating the first slot with the first end so that (a) the first platform is fixedly attached to the bar with a predetermined first orientation relative to the bar, and (b) the first platform can neither rotate nor translate relative to the bar, and also mating the second slot with the second end so that (a) the second platform is fixedly attached to the bar with a predetermined second orientation relative to the bar, and (b) the second platform can neither rotate nor translate relative to the bar.

A clubfoot device can be assembled by providing a kit as described herein, attaching the first platform to the bar by mating the first end with the first slot, and attaching the second platform to the bar by mating the second end with the second slot. Also, one can determine whether the first or third orientation is the therapeutically preferred orientation for the first platform relative to the bar and attach the first platform to the bar in the therapeutically preferred orientation. Likewise, one can determine whether the second or fourth orientation is the therapeutically preferred orientation for the second platform relative to the bar and attach the second platform to the bar in the therapeutically preferred orientation.

We claim:

1. A kit for treating clubfoot in a patient, the kit comprising:
   a first platform;
      the first platform defines a first slot having a longitudinally aligned central axis extending therethrough,
      a second slot having a longitudinally aligned central axis extending therethrough, and
      a first locking hole;
   a second platform; and
      the second platform defines a third slot having a longitudinally aligned central axis extending therethrough,
      a fourth slot having a longitudinally aligned central axis extending therethrough, and
      a second locking hole;
   wherein the longitudinally aligned central axis of the first slot is perpendicular to the longitudinally aligned central axis of the second slot;
   a bar having a first end and a second end;
      the bar comprises a flexible first cantilever having a first button proximate a first end and a flexible second cantilever having a second button proximate a second end,
      the first button sized and shaped to mate with the first locking hole when the first slot mates with the first end, and
      the second button sized and shaped to mate with the second locking hole when the second slot mates with the second end.

2. The kit according to claim 1 wherein the first locking hole is disposed at an intersection of the first and second slots.

3. The kit according to claim 1 wherein the second locking hole is disposed at an intersection of the third and fourth slots.

4. The kit according to claim 1 wherein the first slot is oriented at approximately 30 degrees with respect to a longitudinal central axis of the first platform.

5. The kit according to claim 1 wherein the second slot is oriented at approximately 60 degrees with respect to a longitudinal central axis of the first platform.

6. The kit according to claim 1 wherein the third slot is oriented at approximately 30 degrees with respect to a longitudinal central axis of the second platform.

7. The kit according to claim 1 wherein the fourth slot is oriented at approximately 60 degrees with respect to a longitudinal central axis of the second platform.

8. The kit according to claim 1 wherein the second slot has a greater length than the first slot.

9. The kit according to claim 1 wherein the fourth slot has a greater length than the third slot.

10. The kit according to claim 1 wherein the longitudinally aligned central axis of the third slot is oriented perpendicularly to the longitudinally aligned central axis of the fourth slot.

11. The kit according to claim 1 wherein the bar includes two discrete 15-degree bends.

12. The kit according to claim 1, wherein the first slot is sized and shaped to mate with the first end of the bar, so that when said slot mates with the first end, the first platform is fixedly attached to the bar with a first orientation relative to the bar.

13. The kit according to claim 12, wherein the first orientation is a 30-degree external rotation relative to a longitudinal anterior-posterior axis of the first platform.

14. The kit according to claim 1, wherein the second slot is sized and shaped to mate with the first end of the bar, so that when said slot mates with the first end, the first platform is fixedly attached to the bar with a second orientation relative to the bar.

15. The kit according to claim 14, wherein the second orientation is a 60-degree external rotation relative to a longitudinal anterior-posterior axis of the first platform.

16. The kit according to claim 1, wherein the third slot is sized and shaped to mate with the second end of the bar, so that when said slot mates with the second end, the second platform is fixedly attached to the bar with a first orientation relative to the bar.

17. The kit according to claim 16, wherein the first orientation is a 30-degree external rotation relative to a longitudinal anterior-posterior axis of the second platform.

18. The kit according to claim 1, wherein the fourth slot is sized and shaped to mate with the second end of the bar, so that when said slot mates with the second end, the second platform is fixedly attached to the bar with a second orientation relative to the bar.

19. The kit according to claim 18, wherein the second orientation is a 60-degree external rotation relative to a longitudinal anterior-posterior axis of the second platform.

* * * * *